United States Patent [19]

Takahashi

[11] 4,126,128
[45] Nov. 21, 1978

[54] ELECTRIC DEVICE FOR THERMALLY STIMULATING AUTONOMIC NERVOUS SYSTEM

[76] Inventor: Haruo Takahashi, 8-11, Haracho 3-chome, Suita, Japan

[21] Appl. No.: 784,626

[22] Filed: Apr. 4, 1977

[51] Int. Cl.² ............................................. A61H 29/00
[52] U.S. Cl. .................................................... 128/24.3
[58] Field of Search .................... 128/24.1, 24.2, 24.3, 128/254, 399, 303.1

[56] References Cited

U.S. PATENT DOCUMENTS

| | | | |
|---|---|---|---|
| 2,274,995 | 9/1966 | Eidus | 128/399 X |
| 2,285,105 | 6/1942 | Bacher | 128/24.3 |
| 2,699,771 | 1/1955 | Ruttger-Pelli | 128/24.1 |
| 3,207,159 | 9/1965 | Tateisi | 128/303.1 |
| 3,595,238 | 7/1971 | Gavrilov et al. | 128/303.1 |
| 3,625,202 | 12/1971 | Oyoshirhara et al. | 128/24.3 |
| 3,667,476 | 6/1972 | Muller | 128/399 |

Primary Examiner—Lawrence W. Trapp
Attorney, Agent, or Firm—Wenderoth, Lind & Ponack

[57] ABSTRACT

A home-use device for promoting health by stimulating thermally the autonomic nervous system, which consists of a head attached to a handle, the head comprises positive characteristic thermistor heaters, a heat conducting path intervened with heat barrier films, and skin contacting elements attached to the underside of the heat conducting path. The heat capacity of the head is determined to allow the temperature of the skin contacting elements to be somewhat higher than the temperature required for mild moxibustion, and the number of heat barrier films in the heat conducting path is adjusted to restrict the heat flow from the thermistor heaters to an amount to nearly compensate the lost heat by conduction from the skin contacting elements to the skin of a human body. Thus, the device can automatically attain to the required temperature for mild moxibustion on contacting to the skin.

13 Claims, 5 Drawing Figures

ELECTRIC DEVICE FOR THERMALLY STIMULATING AUTONOMIC NERVOUS SYSTEM

BACKGROUND OF THE INVENTION

The present invention relates to a device for promoting health by thermally stimulating the autonomic nervous system.

As is well known in the oriental medical world, that acupuncture and moxibustion are very effective in promoting health and in curing muscular pains and mental disorders by giving stimulation to the autonomic nervous system, whereby internal endocritic secretion is promoted and visceral organs are activated, since these are governed by the autonomic nervous system. Although these methods are known to be very effective, special skills are required in the practice of acupuncture, and a knowledge of the exact positions for application is also necessary in both acupuncture and moxibustion. While the application of acupuncture is too difficult to be done at home owing to the special skills required, moxibustion can be applied comparatively easily when the points of application on the body surface are taught by men skilled in the art. Therefore, moxibustion has long been adopted as a home method for promoting health and for curing disorders.

However, moxibustion produces artificial burns at the points of application on the skin, and although the burn is effective in producing a comparatively long-lasting effect, it also leaves scars on the skin, which is an apparent defect of the method. Therefore, some improved methods for moxibustion have been devised such as the so-called "Onkyu," i.e., mild moxibustion, in which a garlic slice or others is made between the moxa and skin, or the burning moxa is removed from the skin before the fire in the moxa reaches the skin and is replaced by using a new one during repeated application.

Such a mild moxibustion method is also found to be as effective as the conventional moxibustion methods, although the former requires more applications.

In recent years, some electric heaters have become available in the market which use no moxa but only transfer heat to the points of moxibustion. These are also found to be effective as devices for stimulating the autonomic nervous system. These electric heaters usually comprise an electric resistance heater and metal gear wheels at the top part of the device, and the heat evolved in the heater is conducted to the gears and to the skin therefrom. However, although the current passed to the electric heater can be controlled by a rheostat, it is dfficult to keep the temperature not too high, and the danger of producing burns on the skin and the fear of producing pain by the too high temperature reached due to the bad control of current are unavoidable. The metal gear wheels at the top part of the device enable it to travel on the skin by their rotation with the transversal movement of the device on the skin, but longitudinal movement can not be effected. The teeth of the gears serve to facilitate the rotation, and also, to reduce the surface area of contact of save the amount of heat transferred to the skin even when it is at too high a temperature. This reduced area of contact of gears reduces the chance of their contacting the spots for moxibustion, which are considered to have only the size of approximately 1 to 2 mm in diameter, and the effectiveness of the device is reduced by such reduction in the chance of contact of the gear teeth to the spots. Owing to such defects as described above, the electric devices are not yet widely used in home as health promoting devices.

SUMMARY OF THE INVENTION

The object of the present invention is to avoid such defects of present electric heating devices for mild moxibustion and to provide a safe and easily usable device for mild moxibustion for home use.

According to the present invention, constant temperature thermistor heaters such as the positive characteristic thermistor heaters made by Murata Seisakusho and called as "Posistors" are utilized in the head of the device, and the heat evolved thereby is conducted via a conducting path having insulation and heat barrier films intervened in the path leading to the skin contact elements. By adjusting the heat capacity of the head including the thermister heaters, the heat conducting path, skin contacting elements, and the synthetic resin cover, the skin contacting elements are made attain a temperature somewhat higher than the temperature required for the mild moxibustion when left untouched, and to reach just the latter temperature when they make contact with and are moved on the skin. The temperature change is enabled by varying the number of sheets of the intervening heat barrier films, and also, by changing the speed of the sliding movement of the skin contacting elements on the skin.

Thus, the device according to the present invention can be constructed to make its skin contacting elements automatically reach a temperature somewhat higher than the temperature required for the mild moxibustion, but not high enough to burn the skin, and to the required temperature by the controlling speed of sliding movement of the device by its operator or user.

Since the device of the present invention automatically attains an appropriate temperature for mild moxibustion while moving over the skin, it can be made to have a wider area of skin contact, and, thus, have more chances of contacting the points of moxibustion than the conventional devices. Therefore the device of the present invention has no necessity of having gear wheels at its top part, but can use protuberances with smooth contact surfaces such as in a semi-spherical form, so that it can become not only able to be moved in any direction on the skin, but also to give better feeling in contact to the skin.

BRIEF DESCRIPTION OF THE DRAWINGS

Further objects and a better understanding of the invention will become apparent from the following description taken with the drawings, wherein.

DETAILED DESCRIPTION OF THE INVENTION

A preferred embodiment of the invention will now be described, by way of example, with reference to the accompanying drawings, but the example does not intend to limit the scope of the present invention.

Figure 1:
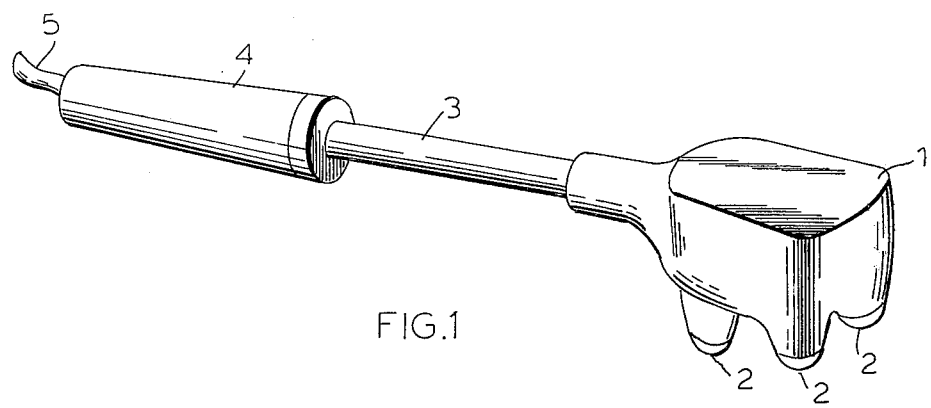
FIG. 1 is a perspective view of the present invention.

FIG. 1 shows the device according to the present invention in a schematic perspective figure, in which the head embedded in a synthetic resin mold 1 and attached with skin contacting elements 2 is connected via a shaft 3 to a handle 4, and through both of them is passed a three cored cable wire 5 from an electric changeover switch circuit (not shown in the figure) to the head 1.

Figure 3:
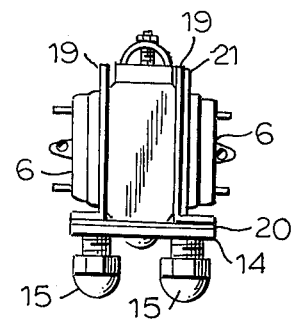
FIG. 3 is an end view of the present invention with the protective cover removed.
Figure 2:
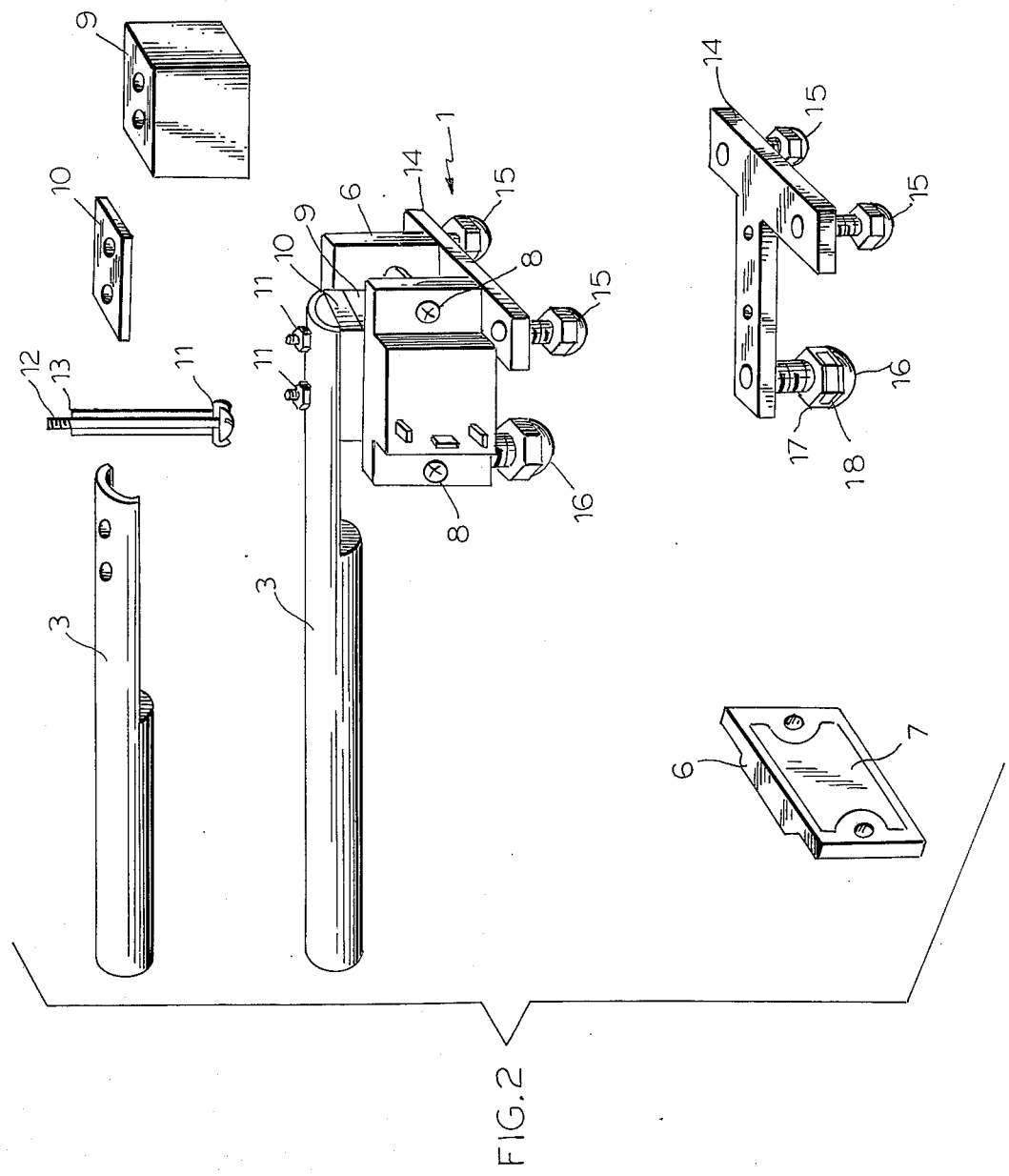
FIG. 2 is an exploded view showing the various internal parts comprising the present invention.

Details of the head 1 and shaft 3 with the synthetic resin cover removed are illustrated in FIG. 2, wherein the parts are also illustrated in a scattered manner in the circumferential part of the figure. Two pieces of positive characteristic thermistor heaters 6 (called as "Posistor" and made by Murata Seisakusho Co., Japan) made with resistance which reversively increases to about 10 fold at 90° C., and having its bare electrode 7 insulated with an insulating film 19 are clamped with two bolts 8 on both sides of an aluminum block 9, which is fixed at its upper surface to the shaft 3 with an intervened heat insulating plate 10 with two bolts 11 consisting of a metal bolt 12 covered with a shrinkable insulating film 13. The lower surface of the block 9 is fixed to a T-shaped copper plate 14 attached with skin contacting elements 15 and 16 by means of the bolts 11. Between the aluminum block 9 and the T-shaped copper block 14 is an insulating film 20 which forms a double electric insulation between the heater and the skin contacting elements 15 and 16 together with the film 19. The skin contacting elements 15 and 16 are each made of a metal rod attached with a semi-spherical shape cap nut 17, on the side surface of which are attached two thermocolor paint marks or labels 18, each of which changes its color at 50° C. or 60° C. FIG. 3 shows the view of the head seen from the vertical top side, wherein the electric insulating films 19 and 20 and a heat barrier film 21 are shown, the number of the latter films 21 being capable of being changed for controlling the heat flow velocity.

When the parts of the head are assembled as described above, and appropriate wiring is completed to the thermistor heaters, the head is embedded in a heat-resistant and electrical insulation resin such as an epoxy resin in a form as shown by 1 in FIG. 1.

Since a skin contacting element can be a metal cap nut with a smooth protruded surface such as in a semi-spherical shape, and its material quality is preferably hard and wear-resistant usually a hard, chrome, electro-plated, semi-spherically shaped cap nut is sufficient.

Whenever a better feeling to the skin is desired, the surface of such a cap nut may be covered with a low frictional synthetic resin layer such as that made of a fluorinated resin.

Figure 4:
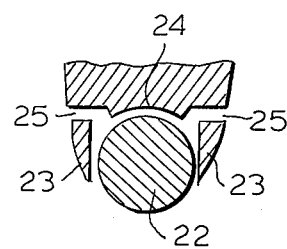
FIG. 4 is a schematic view of an embodiment wherein rollers are provided instead of fixed contact elements.

Also, when a better displacement on the skin is desired, the skin contacting element may have a ballbearing type head such as illustrated in FIG. 4, wherein a ball 22 is rotatably sustained in a cage with side walls 23 and a base 24 while small holes 25 are perforated in the walls 23 to facilitate the cleaning of the ball part.

Any number of skin contacting elements may be selected to make the device suitable for use, but in the present embodiment, a reversed triangular arrangement of 3 elements is selected with two smaller diameter elements in the forward positions and a larger diameter one spaced a little behind the others, so that stability of the sliding movement of the head on the relatively flat surface of a human body can be obtained by the three point contact, and in a narrow hollow place such as that around the eye, the two smaller elements at the top of the head can be used conveniently. The large diameter element at the back may have a taller height, which will facilitate its good contact with the skin.

Figure 5:
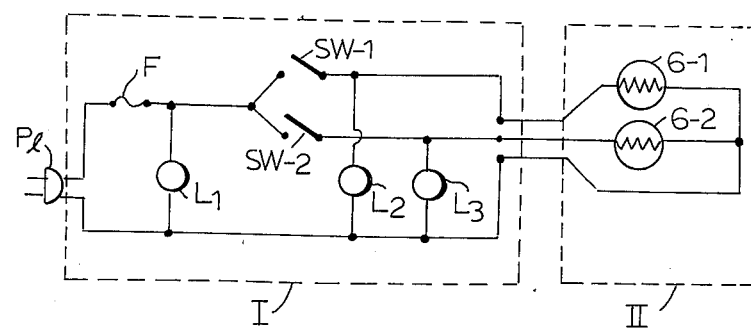
FIG. 5 is an electrical circuit diagram for the present invention.

The electric current passing to the thermistor heaters in the head can be switched by means of various electric circuits. An example is shown in FIG. 5, wherein thermistors 6-1 and 6-2 have a different number of heat barrier plates; P1 denotes a plug, L1, L2, and L3 signal are neon lamps; Sw-1 and Sw-2 are switches; and F is a fuse.

In the present preferred embodiment, the thermistor heaters 6-1 and 6-2 are similar ones with a final constant temperature reached of 90° C., but 6-1 has three heat barrier plates made of a terephthalate film with the thickness of 100 mil, while 6-2 has no film other than an insulating film.

The whole size of the head part of the device has been selected so as to have a heat capacity which allows the final temperature of the skin contacting elements in both cases of passing current to 6-1 and 6-2 be 70° C. when they are left untouched. However, when the skin contacting elements are moved slowly in contact with the skin, they are cooled by the skin to a temperature of about 50° C. for the thermistor heater 6-1 and to a temperature of about 55° C. for 6-2, since the speed of supply of the dissipated heat by conduction to the skin is different in 6-1 and 6-2. The former temperature gives a refreshing feeling to the skin of thin thickness such as that on the face, and the latter temperature is a little hot but is suitable to apply to skins having thick thickness such as those in the head and at the soles of the feet. These temperatures also vary with the speed of sliding movement of the skin contacting elements on the skin. A quick sliding movement is suitable when the skin contacting elements have become hot, since more cooling is effected by the quicker sliding, while slow sliding is suitable for contacting elements at a mild temperature.

Since the temperature of the thermistor heaters is constant at 90° C. during the time the current is passed, and the heat capacity of the head is selected to be of such a magnitude as to allow the maximum temperature during no touching to be not higher than 70° C., and, moreover, since a suitable number of heat barrier films are intervened in the heat conducting path, the temperature of the skin contacting elements of the present invention can be maintained in the temperature range of 50° to 60° C. during its sliding movement in contact with the skin.

What I claim is:

1. An electric device for thermally stimulating the autonomic nervous system, said device comprising:
   a plurality of positive characteristic thermistor heaters spaced from each other;
   heat conducting means between said heaters for regulating the flow of heat from said heaters;
   skin contacting means attached to said heat conducting means for contacting the skin of a person, stimulating the skin, and transmitting heat from said heaters through said conducting means to the skin; and
   said heat conducting means permitting sufficient heat to reach said contacting means to raise said contacting means to a temperature higher than that required for mild moxibustion and said heat conducting means further being able to control the amount of heat from said heaters to said contacting means to compensate for the heat lost from said contacting means when said contacting means is contacting skin.

2. A device as claimed in claim 1, wherein a head covering surrounds said heaters, said heat conducting means and at least a portion of said skin contacting means.

3. A device as claimed in claim 2, wherein said head covering is comprised of a heat resistant and electrically insulative resin.

4. A device as claimed in claim 2, wherein said head covering is an epoxy resin.

5. A device as claimed in claim 2, further comprising a handle connected to said heat conducting means.

6. A device as claimed in claim 1, wherein said heat conducting means is comprised of:
   a metal block having two sides between said heaters;
   a top plate member at the top of said block;
   a bottom plate member at the bottom of said block, and connected to said skin contacting means; and
   electric insulation and heat barrier means between said heaters and said block and between said heaters and block and said bottom plate for electrically insulating said heaters from said block and for permitting only determined amounts of heat from said heaters to reach said block and bottom plate.

7. A device as claimed in claim 6, wherein:
   said block is comprised of aluminum;
   said bottom plate is T-shaped and comprised of copper.

8. A device as claimed in claim 6, wherein said electrical insulation and heat barrier means is comprised of:
   a first electrical insulation member between each of said heaters and said blocks;
   a second electrical insulation member between said block and bottom plate; and
   at least one heat barrier means between at least one of said heaters and said block for governing the amount of heat from said heater which reaches said block, said bottom plate and consequently said skin contacting means.

9. A device as claimed in claim 2, wherein said skin contacting means is comprised of a plurality of stationary projections with smooth, semi-spherical ends connected to said heat conducting means.

10. A device as claimed in claim 9, wherein said semi-spherical ends have a low-frictional synthetic resin coating thereon.

11. A device as claimed in claim 2, wherein said skin contacting means is comprised of three projections in a triangular arrangement connected to said heat conducting means, two projections of equal size and length at one end and one projection larger in size and length than the other two at the other end.

12. A device as claimed in claim 2, wherein said skin contacting means is comprised of a plurality of stationary projections connected to said heat conducting means, and each projection having a rotatable ball at the end thereof.

13. An electric device for thermally stimulating the autonomic nervous system, said device comprising:
   at least one positive characteristic thermistor heater;
   heat conducting means adjacent said heater for regulating the flow of heat from said heater;
   skin contacting means connected to said heat conducting means for contacting the skin of a person, stimulating the skin, and transmitting heat from said heater through said conducting means to the skin; and
   said heat conducting means permitting sufficient heat to reach said contacting means to raise said contacting means to a temperature higher than that required for mild moxibustion, and said heat conducting means further being able to control the amount of heat from said heater to said contacting means to compensate for the heat lost from said contacting means when said contacting means is contacting skin.

* * * * *